United States Patent [19]

Amselem

[11] 4,097,482
[45] Jun. 27, 1978

[54] 5-0-CYANOBENZYL-4,5,6,7-TETRAHYDRO-THIENO[3,2-c]PYRIDINE MALEATE

[75] Inventor: Armand Amselem, Toulouse, France

[73] Assignee: Centre d'Etudes Pour L'Industrie Pharmaceutique, Toulouse, France

[21] Appl. No.: 703,837

[22] Filed: Jul. 9, 1976

[30] Foreign Application Priority Data

Aug. 6, 1975 France .................. 75 24486

[51] Int. Cl.² .......................................... C07D 513/04
[52] U.S. Cl. ...................... 260/294.8 C; 260/294.9; 260/295 S; 424/256
[58] Field of Search .................. 260/294.8 C; 424/256

[56] References Cited

U.S. PATENT DOCUMENTS 3,969,358  7/1976  Amselem ............... 260/294.8 C
4,051,141  9/1977  Castaigne .............. 260/294.8 C Primary Examiner—Alan L. Rotman
Attorney, Agent, or Firm—Young & Thompson

[57] ABSTRACT

The present invention relates to pyridine derivatives having the formula:

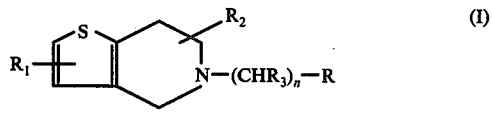

in which:
R is a radical selected from a phenyl radical mono- and polysubstituted with a group selected from the aryl, carboxy, alkoxycarbonyl, cyano, hydroxymethyl and ethylenedioxy groups; a styryl, thienyl and benzhydryl radical optionally mono- and polysubstituted with a group selected from halogen, lower alkyl, lower alkoxy, aryl, nitro, amino, sulfonylamino, carboxy, alkoxycarbonyl, cyano, hydroxymethyl and methylenedioxy;

$R_1$ and $R_2$ represent each a group selected from hydrogen, halogen, hydroxy, lower alkyl, lower alkoxy, nitro and amino;

$R_3$ represents a group selected from hydrogen, halogen, hydroxy, lower alkyl, lower alkoxy, nitro and amino; and $n$ is an integer from 1 to 15, and in which the symbols $R_3$ may have different meanings in each radical $CHR_3$ when $n$ is greater than 1,
and their inorganic and organic acid addition salts and quaternary ammonium derivatives, particularly 5-o-cyanobenzyl-4,5,6,7-tetrahydrothieno[3,2-c]pyridine maleate.

Said derivatives are therapeutically valuable in view of their anti-inflammatory and vasodilator activities and their inhibitor action on blood-platelet aggregation.

1 Claim, No Drawings

5-o-CYANOBENZYL-4,5,6,7-TETRAHYDRO-THIENO[3,2-c]PYRIDINE MALEATE

U.S. Pat. application Ser. No. 660,248 discloses tetrahydrothieno[3,2-c]pyridine derivatives corresponding to the following formula:

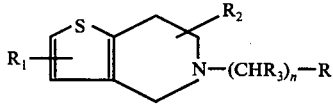

in which R represents hydrogen or a phenyl or benzoyl radical optionally substituted with at least a halogen atom or a lower alkyl, lower alkoxy, nitro, amino or sulfonylamino group; $R_1$ and $R_2$ represent each at least an atom or group selected from hydrogen, halogen and a hydroxy, lower alkyl, lower alkoxy, nitro and amino group; $R_3$ represents hydrogen, halogen or a hydroxy, lower alkyl, lower alkoxy, nitro or amino group and $n$ is zero or an integer from 1 to 15, and the symbols $R_3$ may have different meanings in each radical $CHR_3$ when $n$ is greater than 1, and their inorganic or organic acid addition salts and quaternary ammonium derivatives.

Applicant has now discovered new derivatives which have valuable therapeutic properties, particularly an inhibitor action on blood-platelet aggregation and anti-inflammatory and vasodilator properties.

Thus, this invention relates to tetrahydrothieno[3,2-c]-pyridine derivatives having the formula:

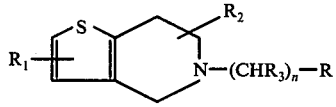

in which:
- R is a radical selected from a phenyl radical mono- and poly-substituted with a group selected from the aryl, carboxy, alkoxycarbonyl, cyano, hydroxymethyl and ethylenedioxy groups; a styryl, thienyl and benzhydryl radical optionally mono- and poly-substituted with a group selected from halogen, lower alkyl, lower alkoxy, aryl, nitro, amino, sulfonylamino, carboxy, alkoxycarbonyl, cyano, hydroxymethyl and methylenedioxy;
- $R_1$ and $R_2$ represent each a group selected from hydrogen, halogen, hydroxy, lower alkyl, lower alkoxy, nitro and amino;
- $R_3$ represents a group selected from hydrogen, halogen, hydroxy, lower alkyl, lower alkoxy, nitro and amino; and
- $n$ is an integer from 1 to 15, and in which the symbols $R_3$ may have different meanings in each radical $CHR_3$ when $n$ is greater than 1, and their inorganic and organic acid addition salts and quaternary ammonium derivatives.

The compounds of this invention may be prepared according to the method disclosed in the aforesaid U.S. Patent Application.

They may be prepared by a process comprising condensing a tetrahydrothienopyridine of the formula:

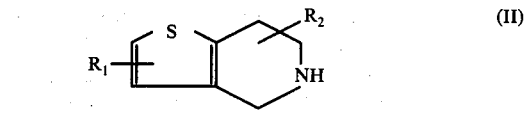

in which $R_1$ and $R_2$ have the above-defined meanings, with a halogen derivative of the formula:

$$X - (CHR_3)_n - R \quad (III)$$

in which X is a halogen atom, R, $R_3$ and $n$ have the above-defined meanings, and, if desired, hydrolysing or reducing an ester function of the resulting material, to give the compound of the formula (I).

The condensation reaction is conducted in an inert solvent medium such as dimethylformamide, acetonitrile, dioxan or toluene.

The following non-limiting Examples are given to illustrate the preparation of the compounds of this invention.

EXAMPLE 1

5-o-Methoxycarbonylbenzyl-4,5,6,7-tetrahydro-thieno[3,2-c]pyridine (Derivative no. 1)

A mixture of thieno[3,2-c]pyridine (3.77 g; 27.8 mmoles), o-methoxycarbonylbenzyl bromide (6.7 g; 29.3 mmoles) and acetonitrile (40 cc) is refluxed during 4 hours. The precipitate obtained on cooling is filtered off, washed with ether and recrystallized from isopropanol (M.p. = 191° C. Yield: 84%).

To a solution of the above compound (35.8 g; 97.2 mmoles) in water (100 cc) and ethanol (400 cc) is added portionwise and while cooling with an ice-bath, 7.5 g sodium borohydride. After stirring overnight at room temperature, the excess borohydride is destroyed by addition of acetone. The resulting material is concentrated in vacuo and the residue is extracted with ether. The organic extracts are washed with water, dried over sodium sulfate and concentrated in vacuo. An equivalent amount of maleic acid in ethanol solution is added to the resulting residual oil. The maleate thus obtained is filtered off, washed with ether and recrystallized from isopropanol (M.p. = 155° C. Yield: 77%).

EXAMPLE 2

5-o-Carboxybenzyl-4,5,6,7-tetrahydro-thieno[3,2-c]pyridine (Derivative no. 2)

A mixture of 5-o-methoxycarbonylbenzyl-4,5,6,7-tetrahydrothieno[3,2-c]pyridine (Derivative no. 1; 19 g; 66 mmoles), ethanol (200 cc) and soda lye (20 cc; d = 1.38) is refluxed during one hour. After cooling, the mixture is accurately neutralized with 6N hydrochloric acid and evaporated to dryness. The solid residue is washed repeatedly with a methylene chloride-ethanol mixture. The washing solutions are combined, dried over sodium sulfate and concentrated in vacuo. The residue is recrystallized from ethanol. (M.p. = 200°-205° C. Yield: 42%).

EXAMPLE 3

5-o-Methoxycarbonylbenzyl-6-methyl-4,5,6,7-tetrahydrothieno[3,2-c]pyridine (Derivative no. 3)

A mixture of 6-methyl-4,5,6,7-tetrahydro-thieno[3,2-c]-pyridine hydrochloride (7.05 g; 37.2 mmoles), o-methoxycarbonylbenzyl bromide (9 g; 39.3 mmoles)

and sodium carbonate (6.05 g; 57 mmoles) in dimethylformamide (100 cc) is stirred during 3 hours at 80° C. After cooling, the inorganic salts are filtered off and the filtrate is evaporated to dryness. The residue is dissolved in ether and the ether solution is washed with water and dried over sodium sulfate, after which the ether is evaporated off. The resulting yellow oil is treated with an equivalent amount of hydrogen chloride gas in ether solution. The hydrochloride is filtered off and recrystallized from isopropyl alcohol-diisopropyl ether (M.p. = 166° C. Yield: 53%).

EXAMPLES 4–11

The following compounds were prepared by a procedure analogous to that described in Example 3.

Derivative no. 4: 5-[(5-Chloro-2-thienyl)-methyl]-4,5,6,7-tetrahydro-thieno[3,2-c]pyridine hydrochloride.

White crystals. M.p. = 200° C

Derivative no. 5: 5-[2-hydroxy-2-(2-thienyl)-ethyl]-4,5,6,7-tetrahydro-thieno[3,2-c]pyridine fumarate.

White crystals. M.p. = 150° C.

Derivative no. 6: 5-(3-o-chlorophenyl-2-propenyl)-4,5,6,7-tetrahydro-thieno[3,2-c]pyridine hydrochloride.

Beige crystals. M.p. = 176° C.

Derivative no. 7: 5-o-cyanobenzyl-4,5,6,7-tetrahydro-thieno[3,2-c]pyridine maleate.

Pale yellow crystals. M.p. = 194° C.

Derivative no. 8: 5-(3,4-methylenedioxy-benzyl)-4,5,6,7-tetrahydro-thieno[3,2-c]pyridine hydrochloride.

White crystals. M.p. = 230°–235° C.

Derivative no. 9: 5-[2-(4-bisphenyl)-2-hydroxyethyl]-4,5,6,7-tetrahydro-thieno[3,2-c]pyridine hydrochloride. White crystals. M.p. = 200°–210° C.

Derivative no. 10: 5-o-hydroxy-methylbenzyl-4,5,6,7-tetrahydrothieno[3,2-c]pyridine.

Pale cream crystals. M.p. = 88° C.

Derivative no. 11: 5-benzhydryl-4,5,6,7-tetrahydro-thieno[3,2-c]-pyridine hydrochloride.

White crystals. M.p. = 250°–260° C. (dec.).

The results of toxicological and pharmacological tests reported below demonstrate the useful activities of the derivatives of the present invention, particularly their inhibitor activity on blood-platelet aggregation and their anti-inflammatory and vasodilator activities.

Thus, the present invention includes also within its scope a therapeutic composition having in particular anti-inflammatory and vasodilator activities and an inhibitor action on blood-platelet aggregation comprising, as active ingredient, a compound of the formula (I) or a pharmaceutically acceptable acid addition salt or quaternary ammonium derivative thereof.

TOXICOLOGICAL INVESTIGATION

Said investigation demonstrated the low toxicity and the good tolerance of the compounds of the present invention.

For indicative purposes, the $LD_{50}/24$ hrs/kg body weight of the animal, determined in mice by the intravenous route, is 92 mg for derivative no. 1, 300 mg for derivative no. 2, 65 mg for derivative no. 3, 165 mg for derivative no. 4, 75 mg for derivative no. 5, 60 mg for derivative no. 6, 45 mg for derivative no. 7 and 65 mg for derivative no. 8.

PHARMACOLOGICAL INVESTIGATION

1. Anti-inflammatory action

Said action was investigated according to two methods.

(a) Localised carrageenin-induced edema method:

A 1% carrageenin solution (0.1 ml) is injected in the metatarsal flexor muscles of the right hind limb of rats at time 0.

The animals of the treated group are additionally administered orally 100 mg/kg of the test derivative, respectively one hour prior to and then simultaneously with the injection of the phlogogenic agent, and then 1 hour and 2.5 hrs thereafter. The percent anti-inflammatory activity with reference to the reference group, as a function of time, is determined by measurements effected with a Roch micrometer at times 0, 1 hour, 2 hours, 3 hours and 5 hours after carrageenin administration. The results obtained with derivatives nos. 1, 4, 5, 8 and 10 are set forth in the following Table.

| DERIVATIVE N° | Percent anti-inflammatory activity | | |
|---|---|---|---|
| | after 1 hour | after 2 hours | after 5 hours |
| 1 | 43 | 50 | 55 |
| 4 | 39 | 47 | 54 |
| 5 | 45 | 53 | 59 |
| 8 | 41 | 51 | 59 |
| 10 | 36 | 48 | 56 |

(b) Ovalbumin-induced systemic edema method

Rats are administered a simultaneous intraperitoneal injection of 1 ml ovalbumin and 0.5 ml of a 1°/ aqueous Evans Blue solution. The animals of the treated group are additionally administered orally 100 mg of the test derivative, 1 hr prior to and simultaneously with ovalbumin administration. The intensity of the phenomenon thus induced is scored according to a scale from 1 to 5, according to the progress of the inflammatory syndrome. Thus are determined the mean intensity of the edema and the percent decrease of the edema reaction with respect to the control group. Said percentages are set forth in the following Table:

| Derivative n° | Percent decrease | |
|---|---|---|
| | after 2 hours | after 3 hours |
| 1 | 51 | 58 |
| 4 | 48 | 53 |
| 5 | 50 | 61 |
| 8 | 54 | 64 |
| 10 | 51 | 62 |

2. Inhibitor action on blood-platelet aggregation

The normally cloudy blood-platelet-rich serum of rats is made clear by addition of adenosine diphosphate which induces aggregation of the blood-platelets. When the same test is effected with serum taken from an animal which has been administered 100 mg/kg of a derivative having an inhibitor effect on blood-platelet aggregation, there is no aggregation of the blood-platelets and the serum remains cloudy. Thus, the inhibitor action on blood-platelet aggregation of the test derivatives may be evaluated by means of a simple spectrophotometric turbidimetric assay.

The tests carried out with groups of five rats (three controls and 2 treated animals) show that the derivatives of the present invention possess a substantial activity and protect the test animals against blood-platelet aggregation in a ratio of the order of 95%.

3. Peripheral and cerebral vasodilator action

This investigation, carried out in rabbits, demonstrated a marked vasodilator action of the derivatives of the invention.

Indeed, administration (perfusion) to the test animals of a solution containing 10 mg/ml per minute, during 20 minutes, produces a substantial vasodilation of the cerebral blood vessels. Indeed, the rheographic investigation demonstrated a marked increase of the cerebral rate of flow associated with a decrease of the peripheral vascular resistance.

It is apparent from the toxicological and pharmacological investigations reported above that the compounds according to the present invention have a good tolerance and possess anti-inflammatory and vasodilator activities and an inhibitor action on blood-platelet aggregation.

The therapeutic composition according to the present invention may be formulated for oral administration as tablets, coated tablets, capsules, drops or syrups. It may also be formulated as suppositories, for rectal administration, and as injectable solutions for parenteral administration.

Each unit dose contains advantageously from 0.025 g to 0.500 g active ingredient, the daily dosage regimen varying within the range from 0.025 g to 1 g active ingredient.

Non-limiting Examples of pharmaceutical formulations of the therapeutic composition of this invention are given below.

EXAMPLE 12 — Tablets

| | |
|---|---|
| Derivative n° 2 | 0.150 g |
| Polyvinylpyrrolidone | 0.010 g |
| Magnesium stearate | 0.005 g |
| Starch | 0.010 g |
| Lactose | 0.025 g |

EXAMPLE 13 — Coated tablets

| | | |
|---|---|---|
| CORE | Derivative n° 5 | 0.100 g |
| | Magnesium stearate | 0.010 g |
| | Kaolin | 0.005 g |
| | Rice starch | 0.020 g |
| | Lactose | 0.015 g |
| COATING | Silica | 0.005 g |
| | Gum arabic | 0.003 g |
| | Gelatin | 0.005 g |
| | Talc | 0.010 g |
| | White wax | 0.002 g |
| | Titanium dioxide | 0.001 g |
| | Tartrazine yellow | traces |
| | Officinal white sugar, sufficient for 1 coated tablet | |

EXAMPLE 14 — Capsules

| | |
|---|---|
| Derivative n° 6 | 0.150 g |
| Magnesium stearate | 0.005 g |
| Starch | 0.010 g |

EXAMPLE 15 — Drops

| | |
|---|---|
| Derivative n° 7 | 1.5 g |
| Flavoured excipient, sufficient to make | 30 ml |

EXAMPLE 16 — Suppositories

| | |
|---|---|
| Derivative n° 9 | 0.125 g |
| Semi-synthetic triglycerides, sufficient to make | 1 suppository |

EXAMPLE 17 — Injectable solution

| | |
|---|---|
| Derivative n° 10 | 0.100 g |
| Isotonic solution, sufficient to make | 3 m |

In view of its anti-inflammatory, vasodilator and blood-platelet aggregation inhibitor properties, the therapeutic composition according to the present invention is usefully administrable for therapeutic purposes.

In short or extended treatments, it is usefully applicable to inflammatory reaction to decrease edema, hypersecretion and exudation and to prevent the organization of the inflammatory lesion. It is applicable in the treatment of post-trauma or post-surgical edema, in plastic surgery, in stomatologic surgery, in the treatment of conditions associated with inflammatory reactions (angina, bronchitis, and the like), in inflammatory or degenerative rheumatism and in acute subarticular conditions.

In addition, in view of its inhibitor effects on blood-platelet aggregation and of its vasodilator effects it is beneficially applicable in the treatment of cardiovascular conditions, both for curative and for preventive purposes; it has a favourable action in the treatment of disorders of the cerebral and peripheral circulatory system and prevents thrombosis-forming complications of atheroma.

Having now described my invention what I claim as new and desired to secure by Letters Patent is:

1. 5-o-cyanobenzyl-4,5,6,7-tetrahydrothieno[3,2-c]pyridine maleate.

* * * * *